(12) United States Patent
Kottler et al.

(10) Patent No.: US 10,074,451 B2
(45) Date of Patent: Sep. 11, 2018

(54) X-RAY INTERFEROMETER

(71) Applicant: CSEM CENTRE SUISSE D'ELECTRONIQUE ET DE MICROTECHNIQUE S.A.-RECHERCHE ET DEVELOPPEMENT, Neuchatel (CH)

(72) Inventors: Christian Kottler, Zurich (CH); Vincent Revol, Zurich (CH)

(73) Assignee: CSEM CENTRE SUISSE D'ELECTRONIQUE ET DE MICROTECHNIQUE S.A.—RECHERCHE ET DEVELOPPEMENT, Zurich (CH)

( * ) Notice: Subject to any disclaimer, the term of this patent is extended or adjusted under 35 U.S.C. 154(b) by 197 days.

(21) Appl. No.: 15/235,173

(22) Filed: Aug. 12, 2016

(65) Prior Publication Data
US 2016/0377559 A1    Dec. 29, 2016

Related U.S. Application Data (62) Division of application No. 13/662,936, filed on Oct. 29, 2012, now abandoned.

(30) Foreign Application Priority Data

Oct. 28, 2011    (CH) .................................... 01753/11

(51) Int. Cl.
*G21K 1/06*       (2006.01)
*G01N 23/20*      (2018.01)
(Continued)

(52) U.S. Cl.
CPC .............. *G21K 1/067* (2013.01); *A61B 6/484* (2013.01); *G01N 23/20008* (2013.01);
(Continued)

(58) Field of Classification Search
CPC .. G01T 1/00; G01T 1/29; G01T 1/295; G21K 1/00; G21K 1/06; G21K 1/067;
(Continued)

(56) References Cited

U.S. PATENT DOCUMENTS

| 7,486,770 | B2 * | 2/2009 | Baumann | ............... | A61B 6/032 |
| | | | | | 378/145 |
| 8,009,797 | B2 * | 8/2011 | Ouchi | .................... | G01N 23/04 |
| | | | | | 378/36 |

(Continued)

FOREIGN PATENT DOCUMENTS

| EP | 2060909 | 5/2009 |
| EP | 2198783 | 6/2010 |
| WO | 98/49546 | 11/1998 |

OTHER PUBLICATIONS

Tilman Donath et al; Inverse geometry for grating-based x-ray phase-contrast imaging; Journal of Applied Physics 106, 054703 (published online Sep. 11, 2009).

(Continued)

*Primary Examiner* — Anastasia Midkiff
(74) *Attorney, Agent, or Firm* — Young & Thompson (57) ABSTRACT

Embodiments relate to an X-ray interferometer for imaging an object comprising: a phase grating for effecting in correspondence with the phase grating geometry a phase shift to at least a part of X-ray incident onto the phase grating; and an absorption grating for effecting in correspondence with the absorption grating geometry absorption to at least a part of X-ray incident onto the absorption grating. The grating period of the phase grating, and the grating period of the absorption grating may be dimensioned such that a detector for X-rays can be placed at a relatively large distance away from the absorption grating such the phase contrast sensi- (Continued)

tivity of the image of the object detected by the detector remains substantially unaffected.

16 Claims, 4 Drawing Sheets

(51) Int. Cl.
    G02B 5/18        (2006.01)
    G02B 27/42       (2006.01)
    G01N 23/20008    (2018.01)
    G02B 27/00       (2006.01)
    A61B 6/00        (2006.01)
    A61B 6/06        (2006.01)

(52) U.S. Cl.
    CPC ..... *G01N 23/20075* (2013.01); *G02B 5/1819* (2013.01); *G02B 5/1838* (2013.01); *G02B 5/1871* (2013.01); *G02B 27/0087* (2013.01); *G02B 27/42* (2013.01); *A61B 6/06* (2013.01); *A61B 6/4035* (2013.01); *A61B 6/4291* (2013.01); *A61B 6/588* (2013.01); *A61B 6/589* (2013.01); *G01N 2223/1003* (2013.01); *G01N 2223/313* (2013.01); *G02B 5/1814* (2013.01); *G02B 2005/1804* (2013.01); *G21K 1/06* (2013.01); *G21K 2201/067* (2013.01); *G21K 2207/005* (2013.01)

(58) Field of Classification Search
    CPC ........... G21K 2201/00; G21K 2201/06; G21K 2201/067; G21K 2201/068; G21K 2207/00; G21K 2207/005; G01N 23/00; G01N 23/20; G01N 23/20008; G01N 23/20075; G01N 23/205; G01N 23/2055; G01N 23/207; G01N 2223/00; G01N 2223/05; G01N 2223/056; G01N 2223/064; A61B 6/00; A61B 6/06; A61B 6/48; A61B 6/484; G02B 5/00; G02B 5/02; G02B 5/0205; G02B 5/021; G02B 5/0215; G02B 5/0252; G02B 5/0263; G02B 5/0273; G02B 5/18; G02B 5/1809; G02B 5/1814; G02B 5/1819; G02B 5/1838; G02B 5/1842; G02B 5/1866; G02B 5/1871; G02B 27/00; G02B 27/0087; G02B 27/10; G02B 27/42; G02B 27/60; G02B 2005/1804
    See application file for complete search history.

(56) References Cited

U.S. PATENT DOCUMENTS

| | | | |
|---|---|---|---|
| 8,781,069 B2* | 7/2014 | Murakoshi | A61B 6/4233 378/36 |
| 9,001,969 B2* | 4/2015 | Murakoshi | A61B 6/4233 378/70 |
| 9,068,919 B2* | 6/2015 | Handa | G01N 23/04 |
| 2009/0012883 A1 | 1/2009 | Kottler et al. | |
| 2010/0009193 A1 | 1/2010 | David et al. | |
| 2012/0140886 A1 | 6/2012 | Murakoshi et al. | |

OTHER PUBLICATIONS

J.C. Elliott et al; X-Ray Microtomography; Short technical note; Journal of Microscopy; vol. 126, Pt 2, May 1982, pp. 211-213.
Martin Engelhardt et al; High-resolution differential phase contrast imaging using a magnifying projection geometry with a microfocus x-ray source; Applied Physics Letters 90, 224101, published online May 30, 2007.
Atsushi Momose; Phase-sensitive imaging and phase tomography using X-ray interferometers; Optical Society of America; Sep. 22, 2003, vol. 11 , No. 19.
Franz Pfeiffer et al; Phase retrieval and differential phase-contrast imaging with low-brilliance X-ray sources; nature physics Advance Online Publication www.nature.comfnaturephysics; Published online: Mar. 26, 2006; doi:10.1038fnphys265.
M. Engelhardt et al; The fractional Talbot effect in differential x-ray phase-contrast imaging for extended and polychromatic x-ray sources; Journal of Microscopy, vol. 232, Pt 1 2008, pp. 145-157; Received Sep. 6, 2007; accepted Mar. 19, 2008.
Franz Pfeiffer et al; Hard-X-ray dark-field imaging using a grating interferometer; Nature Materials vol. 7 Feb. 2008; www.nature.comfnaturematerials.
Noda, Daiji et al: "Fabrication of large area diffraction grating using LIGA process", Microsystem Technologies; Micro and Nanosystems Information Storage and Processing Systems, Springer, Berlin, DE, vol. 14, No. 9-11, Feb. 28, 2008, pp. 1311-1315.
Wen, Han et al. : "Theory of oblique and grazing incidence Talbot-Lau interferometers and demonstration in a compact source x-ray reflective interferometer", OptiCS Express, vol. 19, No. 25, Nov. 23, 2011 pp. 25093-25112.
Bech, Martin et al.: "Soft-tissue phase-contrast tomography with an x-ray tube source; Soft-tissue phase-contrast tomography", Physics in Medicine and Biology, Institute of Physics Publishing, Bristol GB, vol. 54, No. 9; May 7, 2009, pp. 2747-2753.
European Search Report EP 12190359 dated Feb. 1, 2013.
Office Action dated Nov. 15, 2013 for corresponding EP Application 12190359.5.
Summary of teleconference with examiner on Mar. 3, 2014 regarding EP office action dated Nov. 15, 2013 for EP Application 12190359.5.

* cited by examiner

X-RAY INTERFEROMETER

CROSS-REFERENCE TO RELATED APPLICATIONS

The present application claims benefit under 35 U.S.C. § 119(a)-(d) of Swiss Patent Application No. 1753/11 filed on Oct. 28, 2011, the disclosure of which is incorporated herein by reference in its entirety.

TECHNICAL FIELD

Disclosed embodiments relate to imaging systems, and to X-ray imaging systems, in particular.

BRIEF DESCRIPTION OF THE DRAWINGS

These and further features of the embodiments will become more clearly understood in the light of the ensuing description of embodiments thereof, given by way of example only, with reference to the accompanying figures, wherein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals and/or letters may be repeated among the figures to indicate identical or analogous elements but may not be referenced in the description for all figures.

DESCRIPTION OF THE RELATED ART

X-ray imaging is of high importance in view of its numerous applications such as, for example, security screening, medical imaging, quality inspection and non-destructive testing.

Conventional X-ray imaging is based on the detection of the material's attenuation contrast of the object being imaged. There is growing need for better resolution, accuracy, and improved frame rate of the generated X-ray image sequence. One method is X-ray phase contrast imaging which provides increased imaging contrast for weakly absorbing materials, as opposed to conventional X-ray imaging for which the obtained image contrast may be insufficient for practical applications. Weakly absorbing materials may include, for example, biological tissue, polymers or fiber composites.

The principle of X-ray phase contrast imaging is based on detecting minute changes in the direction of propagation, which are caused by refraction of the X-rays passing through a phase shifting object. Equivalent to refraction in the visible light range, the change in direction is proportional to the local gradient in phase shift. It should however be noted, that the refractive power of matter for X-rays is many orders of magnitude weaker than for light in the visible spectrum. Refraction of X-rays may cause a deflection angle in the order of a few micro-radians. In X-ray phase contrast imaging it is the material's refraction index rather than the absorption coefficient which is responsible for the image contrast.

X-ray phase contrast imaging may for example be based on the approach using a Talbot-Lau or the Talbot grating interferometer. A Talbot-Lau interferometer can be used to retrieve quantitative phase images with polychromatic and incoherent X-ray sources, such as X-ray tube sources. The essential part of the interferometer includes two gratings placed between the object and the image detector. The first grating is positioned upstream to the second grating with respect to the X-ray source. Consequently, the first grating is positioned between the second grating and the X-ray source, and the second grating is positioned between the image detector and the first grating. The phase grating is herein referred to as "phase grating", and the second grating is herein referred to as "absorption grating". It should however be noted that the term "phase grating" should by no means to be construed as effecting only a phase shift. Furthermore, the term "absorption grating" should by no means to be construed as only effecting absorption on incident radiation. Correspondingly, the phase grating may, for example, absorb incident radiation, whilst the absorption may, for example, effect phase shifting on incident radiation.

These gratings act as an array of collimating slits whose transmission properties strongly depend on the relative position of the two gratings relative to each other and the radiation angle of incidence on them. Since the angle of incident depends on the refractive powers exhibited by the object on the incident radiation, any local phase gradient caused by the object causes a local change in intensity that may be recorded by the detector.

X-ray phase contrast imaging using the principles of a Talbot-Lau interferometry can thus employ state-of-the-art X-ray equipment such as high power X-ray tube sources and digital image sensors as detectors. As a consequence, X-ray phase contrast imaging may be compatible with a variety of X-ray imaging applications such as scanning, tomography (e.g., Computer-Tomography) and radiography. Documents that related to interferometry are discussed below.

Momose discloses in "Phase-sensitive imaging and phase tomography using X-ray interferometers", Optics Express, Vol. 11, No. 19, 22 Sep. 2003, that it is a characteristic of the Talbot effect that one can observe the appearance and disappearance of the image corresponding to the pattern of the grating along the optical axis. Talbot interferometry employs two gratings. One grating (G2) is placed at a position where the pattern of the other grating (G1) is reproduced by the Talbot effect. Moiré fringes are generated by superposition if the two gratings are slightly inclined. The differential phase caused by an object placed in front of G1 is detected by moiré-fringe bending.

Pfeiffer, Weitkamp, Bunk and David disclose in "Phase retrieval and differential phase-contrast imaging with low-brilliance X-ray source", Nature Physics, 26 Mar. 2006, doi: 10.1038/nphys265, that the total exposure time of the detector can be greatly reduced by using a more efficient detector, decreasing the distance between the source and the object, and using standard rotating anode X-ray generators with a power of a few kW.

European Patent application No. EP2060909 to Kottler et al., entitled "Interferometer device and method" discloses an interferometer device comprising an electromagnetic radiation source emitting radiation; a phase grating having a first aspect ratio; an absorption grating having a second aspect ratio; and a detector. The electromagnetic radiation source, the phase grating, the absorption grating and the detector are radiatively coupled with each other. The absorption grating is positioned between the detector and the phase grating; the electromagnetic radiation source is positioned in front of the source grating; and the phase grating is designed such to cause on at least one wavelength of radiation passing through the grating bars a phase shift ([Delta][Phi]) of less than [pi] relative to radiation passing between the grating bars with respect to the at least one wavelength.

International patent application no. WO9849546 to J. F. Clauser, entitled "ultrahigh resolution interferometric x-ray imaging" discloses a system that may operate in any of the following three modes: "geometric-shadow mode", "amplitude-interferometric mode", and "phase-interferometric mode". The two interferometric modes, in turn, are each a multiplicity of discretely definable modes, and geometric-shadow mode is a limiting case of one amplitude-interferometric mode. Elimination of image blur by scatter is featured by all three modes. Clauser discloses that the system also may employ any of three methodologies—absorption contrast imaging, refractive-index gradient contrast imaging, or element-selective contrast imaging. The choice of mode depends to some extent on the choice of methodology and/or on the system's application. Geometric-shadow mode is used only for absorption contrast. Either of the interferometric modes gives refractive-index contrast, and/or element-selective contrast. Additionally, the system can employ more than two methodologies simultaneously, and can produce two independent images simultaneously from a single x-ray exposure, e. g. one that shows only refractive-index-gradient contrast and one that shows only absorption contrast.

J. C. Eliott and S. D. Dover disclose in "X-ray microtomography", Journal of Microscopy 126, 211-213, 1982, a microscope system which is based on the principles of computerized axial tomography for determining the distribution of the X-ray absorption coefficient in a slice from a solid object without cutting sections. Furthermore, an application is disclosed to determine the distribution at a resolution of about 15 µm through a shell of about 0.5 mm diameter.

Engelhardt, Kottler, Bunk, David, Schroer, Baumann, Schuster and Pfeiffer disclose in "The fractional Talbot effect in differential x-ray phase-contrast imaging for extended and polychromatic x-ray sources" simulations explaining why an interferometer could be combined with polychromatic laboratory x-ray sources and that the distance between the phase and absorption grating of the interferometer is not generally limited by the width of the photon energy spectrum.

Engelhardt, Baumann, Schuster, Kottler, Pfeiffer, Bunk and David disclose in "High-resolution differential phase contrast imaging using a magnifying projection geometry with a microfocus x-ray source" in Applied Physics letter 90, 224101 (2007), that differential x-ray phase contrast imaging using a grating interferometer in combination with a magnifying cone beam geometry using a conventional microfocus x-ray tube effects a magnifying cone beam setup.

Donath, Chabior, Pfeiffer, Bunk, Reznikova, Mohr, Hempel, Popescu, Hoheisel, Schuster, Baumann and David disclose in "Inverse geometry for grating-based x-ray phase-contrast imaging", Journal of Applied Physics 106, 054703 (2009), a setup for CT applications, where the object is positioned behind the phase grating.

In the above-mentioned phase contrast imaging methods and/or systems, magnification may be achieved by altering the position of the imaged object further away from the phase grating, i.e., closer to the X-ray source. However, moving the object away from phase grating towards x-ray source may result in a decrease of phase contrast sensitivity attainable by the employed phase contrast imaging system and method.

The description above is presented as a general overview of related art in this field and should not be construed as an admission that any of the information it contains constitutes prior art against the present patent application.

DESCRIPTION OF EMBODIMENTS

One of the objects of the disclosed embodiments may be to provide an X-ray interferometer that is operative to image a object such that the transverse or linear dimensions of the obtained image of the object are by multiplicative factor M higher than the lateral or linear dimensions of the object itself, at least to a value meeting the constraints imposed by the spatial resolvability of X-ray interferometer. In other words, the X-ray interferometer and imaging method may be operative to attain a multiplicative factor at least up to a value for which the spatial resolvability of the phase contrast imaging system is reached, i.e., two adjacent dots can still be rendered separately on the image.

Furthermore, according to embodiments, the X-ray interferometer may be operative such that for any of the multiplicative value M, the required detection phase contrast sensitivity is not negatively affected, e.g., for at least some practical X-ray imaging applications.

This object is achieved with an X-ray interferometer that comprises an X-ray source, a phase grating, an absorption grating and a detector. The phase grating is positioned between the X-ray source, and the absorption grating is positioned between the phase grating and the detector. The phase grating, the absorption grating and the detector are located downstream to the radiation direction of the X-ray source such that they are optically coupled with each other, i.e., they are positioned in radially symmetrical alignment in respect of a mutually shared optical axis. An object to be imaged may be positioned between the X-ray source and the phase grating such that at least some of the radiation that can be emitted by the X-ray source is incident onto the object.

According to embodiments, the detector is positioned at a distance from the absorption grating such to obtain a detectable or measurable magnification of one or more portions of the imaged object. The detector may thus for example be positioned at a distance from the absorption grating such that, on the one hand, magnification is obtained whilst the X-ray flux incident on the detector is still sufficient to be measurable by the detector. In addition, the distance between the detector and the absorption grating may be chosen such that the magnified portion of the object is still fully resolvable by the detector.

It follows from the above that the planar dimensions, perpendicular to the optical axis, at least of the absorption grating may be smaller than the planar dimensions, also perpendicular to the optical axis, of the detector's sensor field.

Otherwise stated, the magnitude of at least some of the imaginary lines drawn between the geometric origin of the absorption grating to an edge point thereof, may be smaller than the magnitude of the parallel, imaginary line(s) respectively drawn between the geometric origin of the detector to an edge point of the latter. The term "geometric origin" as used herein refers to the intersection point of the optical axis with the corresponding optical element. Consequently, the absorption grating may only partially extend over the sensor field of the detector. Therefore, most or all of the X-ray radiation that may emanate from the absorption grating may be incident onto the detector's sensor field. In embodiments, the detector's sensor field scales with the multiplicative factor M.

It suffices that the planar extensions of the absorption grating and/or of the detector may planarly extend or have lateral dimensions perpendicular to the optical axis such to cover or extend over all of the object's cross-sectional planes that are also perpendicular to the optical axis. However, these planar extensions do not need to cover the lateral extensions of the entire detector, which can be significantly larger than the object size in order to be operative to render an image representing a magnification of the object. In embodiments, at least most or all of the X-ray radiation emanating from the object may be incident onto the phase grating and propagates towards the absorption grating, and at least most or all of the X-ray radiation emanating from the absorption grating may be incident onto the detector's sensor field.

A reduction in the required lateral dimension of the gratings may in some embodiments be advantageous in terms of their fabrication because the larger the grating, the more difficult it is to obtain homogeneous diffraction characteristics. Moreover, the handling, manipulation and alignment of smaller gratings are less demanding than with comparably larger area gratings. In view of the aforesaid, the costs for the X-ray interferometer according to embodiments may be comparably reduced.

Considering for example that the object size extends in the x-direction and y-direction to a few centimeters like, e.g. about 20 cm, the corresponding lateral dimensions of the absorption grating may thus planarly extend from, e.g., about at least 20 cm to, e.g., up to about 25 cm. To remove any semblance of doubt, it should be noted that the term "emanating radiation", as well as grammatical variations thereof may also relate to or include radiation diffracted and/or refracted from an X-ray source. Therefore, depending on the desired multiplicative factor M of a portion of the object, the required maximal width of the absorption grating may be smaller than the maximal width of the detector by a factor of, for example, about at least 1.5, about at least 2, about at least 2.5, about at least 3, or about at least 10.

Thus, according to embodiments of the invention, phase contrast images may be obtained that provide a magnified image of at least a portion of the imaged object, wherein the information shown by the magnified image may be resolvable by the detector, whilst the X-ray flux incident onto the detector may remain substantially unchanged or even increase. Furthermore, the planar extensions of the absorption grating may be smaller than the planar extensions of the detector down to the planar extensions of the object in the x-y plane. A decrease in the planar extensions of the absorption grating correspondingly may reduce the required investment in materials and manufacturing time. Moreover, the complexity of the production facility for the manufacturing of the absorption may be reduced.

Objects that may be imaged by the X-ray interferometer in accordance with embodiments may include, for example, any type of specimen, biological tissue (e.g., skin tissue, muscle tissue, vascular tissue, organ tissue, cancerous tissue), polymers, fibre composites, or any other material or composition of materials having, e.g., a density that is lower than that of osseous tissue of Vertebrates, e.g., having a density being about equal or less than about 1.56 $g/cm^3$, less than about 1.25 $g/cm^3$, less than about 1.15 $g/cm^3$, less than about 1.06 $g/cm^3$, less than about 1 $g/cm^3$, less than about 0.9 $g/cm^3$, or less than about 0.85 $g/cm^3$. It should be noted that the latter statement relating to density should by no means to be construed as limiting. The X-ray interferometer may additionally or alternatively also be operative to image objects having a density that may be equal or higher than that of osseous tissue of Vertebrates. Correspondingly, the X-ray interferometer may be operative to image tissue having a density that is higher than about 1.56 $g/cm^3$.

The X-ray interferometer may be employed in various applications, for example, in Computer-Tomography (CT) for three-dimensional visualization inside objects with resolutions down to the micrometer range or even below. Applications include, for example, medical and/or industrial applications and/or any other application that may require imaging of cross-sectional planes or slices of object. Medical applications may include, for example, mammography. Industrial applications may relate, for example, to non-destructive testing of material.

SUMMARY OF EMBODIMENTS

Embodiments are related to an X-ray interferometer for imaging an object by irradiating the object with X-rays emitted, e.g., by a point X-ray source at a given radiation energy. The X-ray interferometer comprises a phase grating for effecting in correspondence with the phase grating geometry a phase shift to at least a part of X-ray incident onto the phase grating; and an absorption grating for effecting in correspondence with the absorption grating geometry absorption to at least a part of X-ray incident onto the absorption grating.

In embodiments, the grating period of the phase grating and/or of the grating period of the absorption grating are dimensioned such that an X-ray detector for imaging the object can be placed at a relatively large distance away from the absorption grating such that for the given radiation energy, the X-ray flux incident onto the detector is substantially non-adversely affected.

In embodiments, the X-ray interferometer further includes the detector for X-rays placed at a relatively large distance away from the absorption grating.

In embodiments, the distance is selected such to allow a detectable divergence of or effect a corresponding image magnification by the phase- and intensity-modulated X-ray emanating from the absorption grating and incident onto the detector.

In embodiments, the X-ray interferometer is a Talbot or Talbot-Lau Interferometer.

In embodiments, the grating periods of the phase grating and of the absorption grating are dimensioned such the detector can be placed at a relatively large distance away from the absorption grating such that for the given radiation energy the phase contrast sensitivity of the image of the object detectable by the detector is substantially non-adversely affected, (e.g., remains substantially the same or may even increase).

In embodiments, respective of a given radiation energy, the grating periods of the absorption grating and the phase grating are dimensioned such that placing the detector at relatively large distance from the absorption grating results in a corresponding increase in the attainable image magnification of an object to be imaged while at the same time the phase contrast sensitivity of an image of the object detectable by the detector and/or the X-ray flux incident on the detector is substantially non-adversely affected (i.e., remains substantially the same or may even increase).

In embodiments, the grating periods of the phase grating and of the absorption grating are dimensioned such that the phase contrast sensitivity of the image of the object detected by the detector of the X-ray interferometer is substantially not adversely affected by placing the detector at a relatively large distance away from the absorption grating.

In embodiments, the lateral extensions of the phase grating, the absorption grating and the detector cover the diverging field size respective of the X-ray emanating from the object when being imaged.

In embodiments, during imaging, the grating periods of the phase and absorption grating can be dimensioned or selected such that the distance between the object and the phase grating can be selected to substantially equal zero.

In embodiments, the phase contrast sensitivity of an image of the object remains substantially equal or increases, compared to the phase contrast sensitivity of an image of at least a part of the object when the distance between the detector and the absorption grating substantially equals 0.

In embodiments, the lateral dimensions of the phase grating, the absorption grating and the detector are such to allow for selecting the distance between the detector and the absorption grating to obtain a corresponding change in the multiplicative factor between the lateral dimensions of the image and the object itself.

In embodiments, the phase contrast sensitivity of the image ranges from about 150 to about at least 300.

In embodiments, wherein the obtainable magnification ranges from greater than 1 to about at least 50.

Embodiments relate to a method for performing phase contrast imaging by employing an X-ray interferometer. In embodiments, the method comprises dimensioning the grating period of the phase grating and of the absorption grating such that a detector can be placed at a relatively large distance away from the absorption grating, in a manner allowing a detectable divergence of the phase- and intensity-modulated X-ray from the absorption grating to the detector, and such that for the given energy, the X-ray flux incident onto the detector during imaging is substantially non-adversely affected.

In embodiments, the method comprises positioning the object at distance from the phase grating which substantially equals zero.

DESCRIPTION OF EMBODIMENTS

Embodiments relate to providing an X-ray interferometer that enables providing an image of an object, wherein the lateral dimensions of the image are by a multiplicative factor higher than the lateral dimensions of the object to be imaged.

It should be noted that the term "coherent" and "monochromatic" as used herein as well as grammatical variations thereof also may also encompass the meaning of the term "substantially coherent" and "substantially monochromatic", respectively.

In many fields of potential applications such as in industry or medicine higher X-ray energies are demanded in order to provide sufficient object transmission. Therefore, by enabling interferometry with, e.g., X-rays emitted from the X-ray source at mean energies of, for example, about at least 20 keV, about at least 40 keV, about at least 60 keV, or about at least 80 keV, the type of materials and objects that can be imaged enabling practical applications is largely increased.

It should be noted that the adjective "equal" as used herein may also encompass the adjective "substantially equal".

It should be noted that although the embodiments are described herein and exemplified with reference to an X-ray interferometer that is based on the principles of a Talbot-interferometer, this should by no means to be construed as limiting. Consequently, embodiments may likewise be implemented based on the principles of, e.g., a Talbot-Lau interferometer. Consequently, in accordance with an embodiment, the X-ray interferometer may include three gratings, e.g., as known in the art. In some embodiments, the X-ray interferometer may optionally include a source grating, which may be positioned between radiation source and phase grating. An object to be imaged may be positioned between source grating and phase grating. Source grating may be operative, for example, to cause radiation emitted by X-ray source to become spatially coherent. The X-ray interferometer may thus embody a Talbot-Lau interferometer.

It should be noted that the term "spatially coherent", as well as grammatical variations thereof, may also encompass the meaning of the term "substantially spatially coherent" or "at least approximately spatially coherent".

Figure 1:
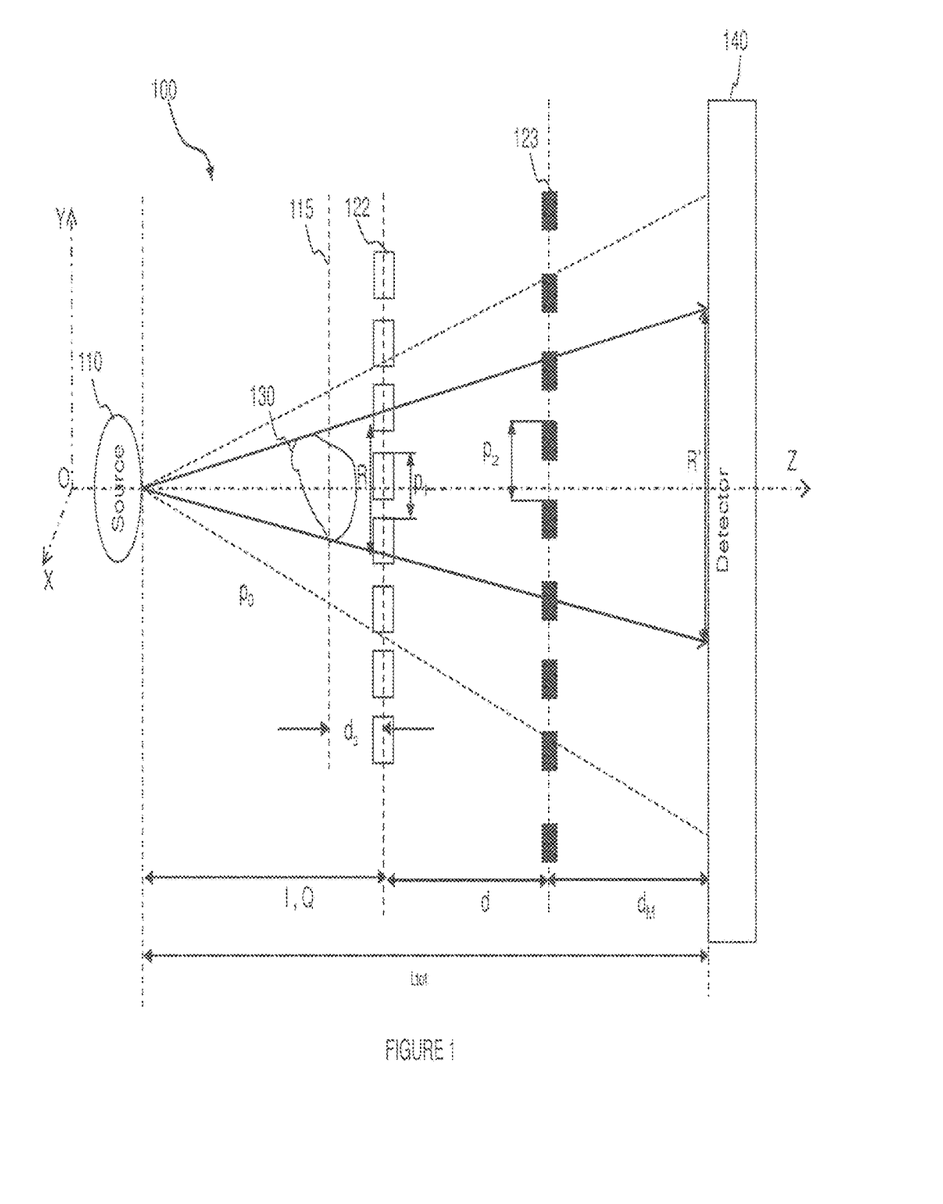
FIG. 1 is a schematic illustration of a setup of an X-ray interferometer, in accordance with an embodiment.

Reference is now made to FIG. 1, which is a schematic illustration of an X-ray interferometer 100, in accordance with an embodiment.

X-ray interferometer 100 may include, for example, an X-ray source 110, a phase grating 122, an absorption grating 123, and a detector 140 that is operative to detect radiation emitted by X-ray source 110.

Phase grating 122 is positioned between X-ray source 110 and absorption grating 123, and absorption grating 123 is positioned between phase grating 122 and detector 140. Phase grating 122 may be manufactured from a phase shifting and substantially non-absorbing material for X-ray such as, for example, silicon. Absorption grating 123 may be made from an X-ray absorbing material such as, for example, gold.

X-ray source 110, phase grating 122, absorption grating 123 and 140 are optically coupled with each other such that radiation emanating from X-ray source 110 is incident onto phase grating 122, absorption grating 123 and detector 140 allowing the imaging of an object 130, which may be positioned between X-ray source 110 and phase grating 123. In other words, X-ray source 110 is operative to emit radiation which may be incident onto phase grating 122 and result in radiation that further propagates from phase grating 122 and is incident onto absorption grating 123. The radiation incident onto absorption grating 123 may subsequently result in radiation that emanates from absorption grating 123 and is incident onto detector 140.

Consequently, if the radiation emitted by X-ray source 110 is responsive to at least some differences in the material of object 130 as well transmissive to the emitted radiation, such differences may be recorded by detector 140, as outlined herein below in greater detail.

X-ray source 110 may be embodied, for example, by an electromagnetic (EM) radiation source that is operative to emit a radiation beam having conical divergence geometry. As a result, X-ray source 110 may provide the effect of a projection magnification M, which can for example be defined as follows:

$$M = \frac{R'}{R} \quad (1)$$

wherein R—denotes the object size of object 130, and R' denotes the size of the image of object 130 projected onto detector 140. In accordance with embodiments, magnification M is higher than 1 and may range, for example, from 1, from about 1.1, or from about 1.5 to about at least 50.

It should be noted that the term "conical" as used herein, as well as grammatical variations thereof, may also encompass the meaning of the term "substantially conical" or "at least approximately conical". Furthermore, the term "point source" as used herein, as well as grammatical variations thereof, may also encompass the meaning of the term "substantially a point source" or "at least approximately a point source".

X-ray source 110 may be embodied, for example, by a point source of radiation such as, for example, a micro-focus X-ray source, e.g., as known in the art. X-ray source 110 may have an output of a W target and be operative to emit light having a focal spot size ranging, for example, from about 0.1 to about at least 3000 µm, when operated at tube voltage of, e.g., 20 to 170 kV and at a tube current of, e.g., about 0.1 µA to about at least 50,000 µA. The X-ray beam angle, measured at the source, may range, for example, from about 35 to about at least 120 degrees.

Grating period of phase grating 122 and absorption grating 123 are herein denoted as $P_1$ and $P_2$, respectively.

$\lambda$—denotes the wavelength of the X-ray emitted by X-ray source 110.

n—denotes the fractional Talbot order $\eta$—denotes the symmetry parameter

M—denotes the multiplicative factor of the image of an object by employing X-ray interferometer 100.

L—denotes the distance between X-ray source 110 and phase grating 122 d—denotes the distance between phase grating 122 and absorption grating 123;

$d_M$—denotes the distance between absorption grating 123 and detector 140,

Q—denotes the maximal distance between phase grating 122 and object 130 (which may be limited by X-ray source 110 or a source grating (not shown)), and $d_s$—denotes the distance between plane 115 which is perpendicular to the optical axis Z and which intersects with the geometric centre of object 130. The said plane 115 is hereinafter referred to as "centre plane" 115.

For the discussion that follows, it is assumed that the widths of phase grating 122 and absorption grating 123 is infinitely small or at least negligible with respect to the distances L, d and $d_M$. It may further be assumed, that the position of object 130 is such that the distance between centre plane 115 and phase grating 122 is infinitely small or at least negligible compared to the distances L, d and $d_M$. It is be assumed that the distance d is small compared to the distances L and $d_M$, i.e., d<<$d_M$ and d<<L. However, the above-outlined assumptions should not be construed as limiting and are thus not a precondition for the operability of X-ray interferometer 100 as outlined herein.

To enable phase contrast imaging of object 130 with X-ray interferometer 100, the following three constraints may have to be met:

$$D_n = n \cdot \frac{p_1^2}{8\lambda} \quad (2)$$

wherein $D_n$ denotes the fractional Talbot distance $$d_n = \frac{L \cdot D_n}{L - D_n} \quad (3)$$

wherein $d_n$ denotes the Talbot distance which is corrected for divergence; and $$\frac{\eta \cdot p_2}{p_1} = \frac{L + d}{L} \quad (4)$$

which defines the condition for beam divergence.

Following equations 1, 2 and 3, the distances L and d can, for example, be parameterised by the X-ray wavelength A, e.g., as follows:

$$d = \frac{n \cdot \eta \cdot p_1 \cdot p_2}{8 \cdot \lambda} \quad (5)$$

$$L = d \cdot \frac{p_1}{\eta \cdot p_2 - p_1} \quad (6)$$

It should be noted that other mathematical terms those outlined herein may be used to express the same physical conditions.

The parameter $\eta$ in these equations reflects the symmetry of the interference pattern between the wavefronts emanating from absorption grating 123. The symmetry depends on the design of phase grating 122, as outlined herein below. In case phase grating 122 is designed such that it shifts incident wavefront by, e.g., $\Delta\phi=\pi$ then $\eta=2$. In case phase grating 122 is designed such that $\Delta\phi<\pi$ (for example $\pi/2$), then $\eta=1$. According to these equations, for given grating periods $P_1$ and $P_2$ of phase grating 122 and absorption grating 123, respectively, the parameters L and d and therefore the overall distance between X-ray source 110 and detector 140 may have to increase, linearly, with increasing X-ray energy emitted by X-ray source 110, to meet the constraints expressed in equations 1) to 3).

According to some embodiments, multiplicative factor M that may be effected by X-ray interferometer 100 may be expressed by the following mathematical term:

$$M = \frac{R'}{R} = \frac{d_M + d + L}{L - d_s} \quad (7)$$

According to embodiments, X-ray interferometer 100 may be operative such that the ratio M, which is also the multiplicative factor, of the size of the image of object 130 on detector 140 to the size of the imaged object 130 is at least M>1. For example, altering the distance $d_M$ results in a corresponding change in the multiplicative factor M. Altering $d_{M1}$ to $d_{M2}$, wherein $d_{M2}>d_{M1}$, results in an increase of the multiplicative factor M and therefore in a lateral magnification. Conversely, altering $d_{M2}$ to $d_{M1}$, results in a decrease in of the multiplicative factor M and therefore in a reduction of the lateral scale of the image or minification. In other words, magnification is achieved at least by positioning detector 140 away from absorption grating 123 and farther downstream of X-ray propagation beam path. Consequently, detector 140 may be physically decoupled from absorption grating 123.

According to embodiments, X-ray interferometer 100 may be operative such that by altering $d_M$ a corresponding change in the multiplicative factor M may be obtained even if the distance $d_s$ remains unchanged. Considering, for example, $d_s$ has any value between 0 to Q, a change of $d_M$ from $d_{M1}$ to $d_{M2}$, wherein $d_{M2} > d_{M1}$ results in an increase of the multiplicative factor M, which is reflected by an image representing a magnification of object 130.

Additionally or alternatively, a change in the multiplicative factor M may be obtained by altering $d_s$, i.e., by changing the distance of object 130 relative to phase grating 122. For example, when altering $d_s$ from $d_{s1}$ to $d_{s2}$, wherein $d_{s1} < d_{s2}$, may result in an increase in the multiplicative factor, and vice versa.

In some embodiments, $d_M$ may be selected up until the maximum value for which X-ray interferometer 100 is operative to render two dots separately on an image of object 130, i.e., magnification M attains a value which is below what is sometimes dubbed "empty magnification".

Phase Contrast or Angular Sensitivity [$rad^{-1}$]:

The phase shift $\Phi$ (x,y) imposed on the wave field by object 130 positioned in the beam path causes a refraction of the beam in x-direction by the angle $\alpha$, which is connected with the differential phase shift $\neq \Phi / \neq x$ by $$\alpha = \frac{\lambda}{2\pi} \frac{\partial \Phi}{\partial x} \quad (8)$$

with the X-ray wavelength $\lambda$ and the beam propagation along the z-direction.

The term "phase contrast or angular sensitivity" (S) as used herein may be defined as the ratio of phase-shift $\Phi$ in the intensity oscillation of the phase scan (normalized to $2\delta$) to the refraction angle á caused by object 130:

$$S \equiv \frac{1}{2\pi} \frac{\Delta \varphi}{\alpha} \quad (9)$$

The measurement of phase contrast sensitivity depends, at least partially, on the relative position of object 130 with respect to phase grating 122 and absorption grating 123 and increases the closer object 130 is put behind phase grating 122, and vice versa.

In some embodiments, the position of object 130 may thus be chosen to at least partially compensate for any reduction in the phase contrast sensitivity of X-ray interferometer 100 that may otherwise occur due to choosing $d_{M2}$ instead of $d_{M1}$, wherein $d_{M2} > d_{M1}$. For example, object 130 may be placed before phase grating 123 in a manner preventing negatively affecting the phase contrast sensitivity that may occur due to alteration the position of object 130 from $d_{M1}$ to $d_{M2}$.

At least partial compensation for possible reduction of phase contrast sensitivity may for example be achieved by correspondingly placing object 130 closer to phase grating 122, i.e., by altering $d_s$ from $d_{s1}$ to $d_{s2}$, wherein $d_{s2} < d_{s1}$. Additionally or alternatively, orientation of object 130 may be chosen such that for a distance $d_{si}$ the average distance of all points of object 130 to phase grating 122 is at least approximately minimized.

At some instances, the phase contrast sensitivity for $d_M > 1$ for X-ray interferometer 100 as opposed to $d_M = 0$ in substantially non-multiplicative or substantially non-magnifying X-ray interferometers may even increase. X-ray interferometer 100 may for example be configured such to be operative to obtain an image of object 130 with a phase contrast sensitivity ranging, for example, from about 25 to about at least 260. For example, the phase contrast sensitivity attainable by X-ray interferometer 100 may be, for example, about at least 25, about at least 50, about at least 120, about at least 160, about at least 200 or about at least 260.

Assuming now, for example, $d_s = 0$; or $d_s \approx 0$; or $d_s << d_M$, $d_s << d$ and $d_s << L$, equation 6 can then be approximated as follows:

$$M = \frac{R'}{R} \approx 1 + \frac{d_M}{L} = \frac{L + d_M}{L} \quad (10)$$

Consequently, the degree of magnification can be selectively adjusted without necessarily having to change the parameters of phase grating 122 and absorption grating 123. Otherwise stated, if $d_s = 0$; or $d_s \approx 0$, or $d_s << d_M$ and $d_s << d$ and $d_s << L$, then for any $d_M > 0$ the obtainable phase contrast sensitivity is at least approximately or substantially maximized compared to when $ds < d_M$, and a corresponding multiplication factor of M>1 enabling practical imaging applications (e.g., M≥2, ≥3, ≥5, or, e.g., M≥10) may be obtainable with X-ray interferometer 100 without necessarily having to compromise on phase sensitivity. Correspondingly, the phase contrast sensitivity may attain a value which is at least approximately equal to the maximal phase contrast sensitivity that may theoretically be obtainable by X-ray interferometer 100 in case object 130 had, theoretically, infinitely small width (measured along optical Z-axis).

Spatial Resolution

The achievable spatial resolvability by interferometer system 100 when imaging object 130 is determined, for example, by the spatial resolution of detector 140 and the focal spot size of X-ray source 110. Furthermore, the achievable spatial resolvability may be limited by the grating period of, e.g., phase grating 122. Once the wave front originating from X-ray source 110 has passed phase grating 122, the information on the local deflection effected on the wavefront by phase grating 122 is limited by or can not be resolved beyond the grating period $P_1$. Thus, a reduced grating period $P_1$ may allow for greater spatial resolvability of the imaged object 130 by interferometer 100, and vice versa. More specifically, attainable magnification M may be restricted to a value for which the spatial resolution in the image plane (not shown) of phase grating 122 is larger than grating period $P_1$ of phase grating 122. The achievable spatial resolvability of two adjacent dots may thus be, for example, about 3 μm or less.

Considering distance X as the spatial resolution of detector 140 (for example, the distance between two adjacent pixels) leads to the following condition: M≤X/$P_1$, i.e., grating period $P_1$ must be smaller than X to be able to attain M>1. As a consequence, if object 130 is positioned as close as possible to phase grating 122 such that $d_s$ equals or at least approximately equals 0, the spatial resolution is limited to the phase grating period $P_1$. If $d_s >> 0$, the limitation of spatial resolvability by phase grating 122 is given by the back-projected period of $P_1$ onto object 130. The back projected period is hereinafter referred to as "$P_{back-1}$". $P_{back-1}$ can be smaller than the grating period $P_1$ and can be expressed, for example, as follows:

$$P_{back-1} = P_1 \cdot ((L - d_s)/L) \quad (11)$$

Therefore, if the application calls for a spatial resolution that is better than (i.e. below that of) grating period $P_1$, the spatial resolution can be improved by moving object 130 away from phase grating 122 ($d_s>0$). However, increasing $d_s$ will be at the expense of the attainable phase contrast sensitivity. The optimal configuration of phase contrast imaging system 100 is thus determined by the specific operation requirement for a particular imaging application.

Spatial Coherence:

The requirement on sufficient spatial coherence for phase contrast imaging system 100 may have to be met. In general, these requirements are fulfilled because the focal spot size of X-ray tube sources typically used in micro CT may be such to be substantially compatible with coherence requirements for practical applications. The focal spot size may for example range from about 0.1 µm to about at least 3000 µm, or range from about 0.1 µm to about at least 50 µm. Furthermore, the magnitude of grating periods $P_1$ and $P_2$ may range, for example, from about 0.05 µm, about 1 µm, or about 1 µm to, e.g., about 10 mm or higher.

Distance $d_M$ between absorption grating 123 and detector 140 is greater than 0 cm and can be up to a few meters such as, for example, about at least 1 mm, about at least 2 mm, about at least 1 cm, about at least 2 cm, about at least 3 cm, about at least 5 cm, about at least 6 cm, about at least 7 cm, about at least 8 cm, about at least 9 cm, about at least 10 cm, about at least 15 cm, about at least 20 cm, about at least 50 cm, about at least 1 m, about at least 1.5 m or about at least 2 m. In some embodiments, X-ray interferometer 100 may be configured such that the position of detector 140 and/or absorption grating 123 are moveable relative to each other enabling selectively setting distance $d_M$ in a manner such that imaging parameters (e.g., phase contrast sensitivity and/or spatial resolution) for an object 130 to be imaged are met. In some embodiments X-ray interferometer 100 may, for example, include a support (not shown) on which detector 140 and/or absorption grating 123 may be mounted for enabling selectively setting, discretely or slidably, distance $d_M$.

Figure 2A:
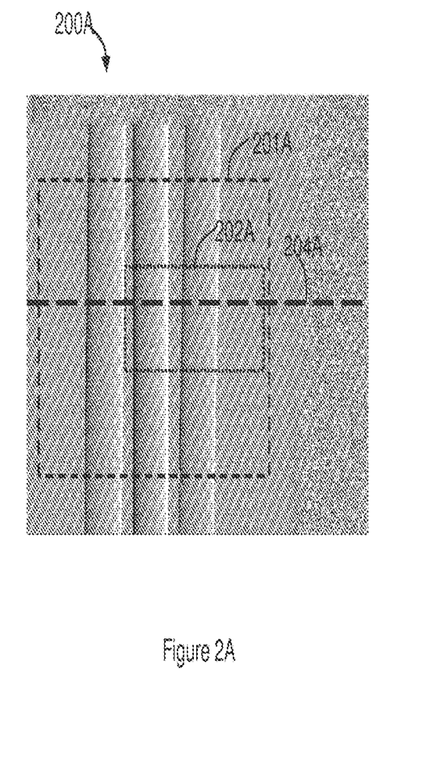
FIG. 2A shows a reference image of an object acquired by employing a substantially non-magnifying X-ray interferometer.
Figure 2B:
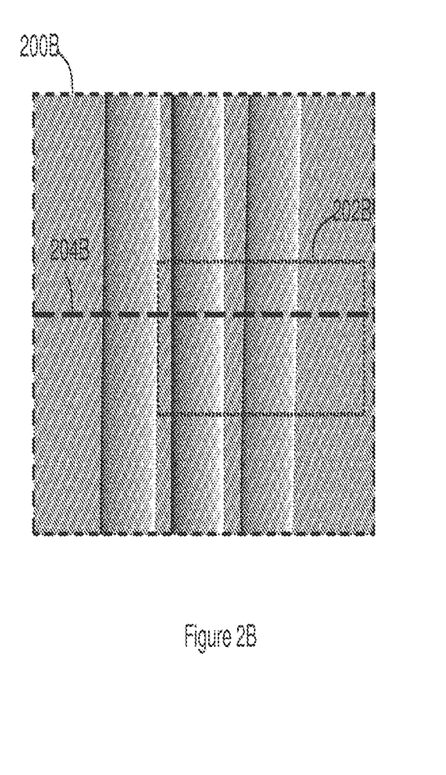
FIG. 2B shows a magnified image of the object acquired by employing an X-ray interferometer, in accordance with an embodiment.
Figure 3A:
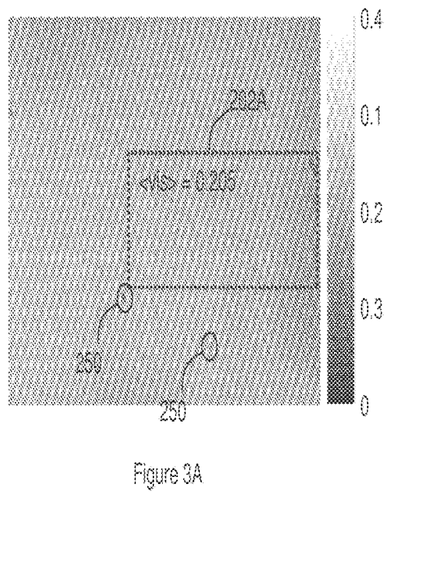
FIG. 3A shows a visibility map of the reference image, in accordance with an embodiment.
Figure 3B:
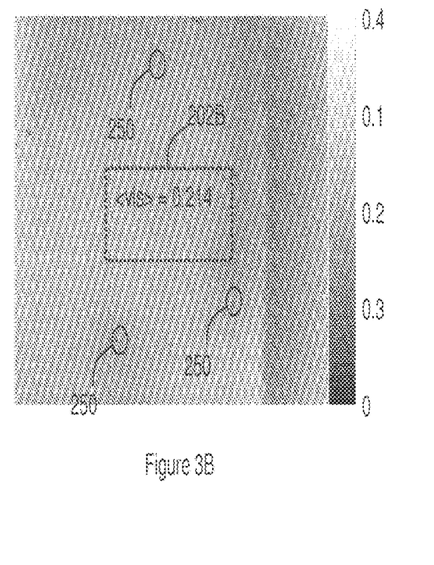
FIG. 3B shows a visibility map of the magnified image, in accordance with an embodiment.

Additional reference is now made to FIG. 2A which illustrates a reference image of object 130 acquired by substantially non-magnifying X-ray interferometer; to FIG. 2B, which illustrates a magnified image of object 130 acquired by X-ray interferometer 100, in accordance with an embodiment; to FIG. 3A, which illustrates a visibility map of the reference image, in accordance with an embodiment; and to FIG. 3B, which illustrates a visibility of the magnified image, in accordance with an embodiment.

Visibility of a Selected Area/Region of Interest of an Image as a Figure of Merit for the Performance of X-Ray Interferometer 100:

With respect to phase contrast imaging, the visibility of an image of object 130 may for example be defined as the relative height between the maximum and minimum intensity of the interference fringes. Accordingly, the measured visibility can be a figure of merit for the performance of the respective X-ray interferometer.

Various techniques may be applied for determining visibility. For example, a phase-stepping procedure may be employed, wherein the visibility can be determined pixel-wise and a map of the visibility over the entire field of view can be obtained. Defects of the gratings cause specific spots of poor visibility on these maps. Such spots, referenced 250, can be identified in the visibility maps shown in FIGS. 3A and 3B.

The quality of the employed gratings determines the visibility attainable by X-ray interferometer 100. The mean value of the visibility over a region of interest of an image may thus be a representative measure for the visibility of the entire image generated by X-ray interferometer 100. The reason therefor is as follows: a wave field downstream of absorption grating 123 continues propagating and forms a first interference pattern at a first period. However, the intensity measured at the pixel of detector 140 is independent of a particular fringe pattern, since detector 140 measures the average intensity over many periods of the fringes. This is true for any M>0 up to a value for which an increased number of details are made visible on the obtained magnified image.

Influence of $d_M$ on Visibility

X-ray interferometer 100 may, in some embodiments, be operative such that the visibility is substantially independent or unaffected by an increase or decrease of the distance denoted $d_M$ between absorption grating 123 and detector 140. In other words, the influence on the visibility by increasing or decreasing $d_M$ is comparably negligible, as outlined herein below in greater detail. In particular, setting $d_m>0$ (e.g., to a distance of, for example, 1 mm to 3 m) as opposed to where $d_M$ substantially equals 0, has a negligible effect on the visibility of the phase contrast images obtainable with X-ray interferometer 100.

Both the substantially non-magnifying X-ray interferometer as well as X-ray interferometer 100 which were respectively employed for generating the images shown in FIGS. 2A and 2B, are based on the Talbot-Lau interferometer principle. However, as already mentioned herein above, this should by no means to be construed as limiting. To implement the Talbot-Lau based interferometer, both the substantially non-magnifying X-ray interferometer as well as X-ray interferometer 100 employ X-ray source 110 which is assumed to have the appropriate focal spot size. Furthermore, detector 140 of X-ray interferometer 100 is operative to provide sufficient spatial resolution so that the multiplicative factor M may only be limited by the grating period $P_1$.

In the examples shown, phase contrast images were acquired for object 130 that is embodied by three rods, each one being made of a different material of plastic. The diameters of each one of the three rods measure about 6 mm. Both images show the same region of interest of the sensor field of detector 140.

A region of interest (ROI) 201A of a non-magnified image 200A of object 130 is magnified by X-ray interferometer 100 which results in a magnified image 200B.

ROI 202A schematically outlines a specific region of non-magnified image 200A for which the visibility is determined. Correspondingly, ROI 202B schematically outlines the boundary of the region of interest of magnified image 200B for which average visibility is determined.

In both images 200A and 200B identical areas of field of views of detector 140 are displayed. Further parameters of the imaging setup were as follows: I equals about 126 cm, d equals about 19.0 cm, $P_1$ equals about 2.6 µm, and $p_2$ equals about 3.0 µm. The focal spot size of X-ray source 110 was about 1 mm. Clearly, second phase contrast image 200B which is taken with $d_M$ equaling about 70 cm shows the rods magnified compared to the case where $d_M$ equals about 0. The attained magnification M equals about 1.48 with respect to the image at $d_M$ equals about 0.

Visibility measurements were performed with the Talbot-Lau interferometer, because an X-ray tube source with a focal spot size of about 1 mm² was used. The source grating that was used had a grating period of equals about 20 µm. Because of the size of the focal spot the spatial resolution may not improve. However, the effect of the distance $d_M$ on the visibility can be analysed appropriately. For the case exemplified hereinabove, the visibility of ROI 205A and ROI 205B equals about 0.205 and equals about 0.214, respectively. Thus, second phase contrast image 200B maintains approximately the same visibility value despite magnification of M>1.3.

Figure 4A:
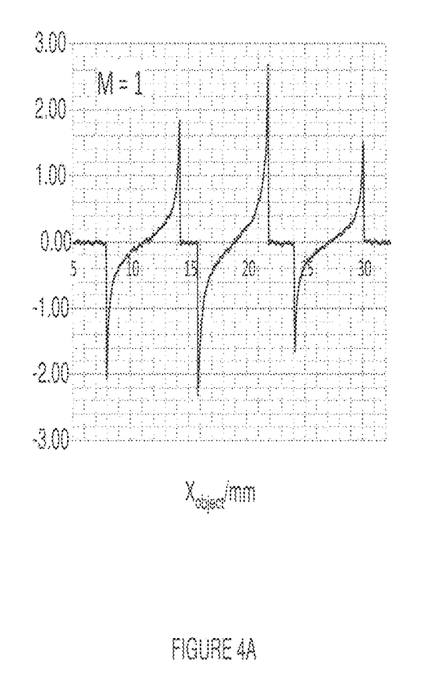
FIG. 4A schematically illustrates the phase contrast signal intensity at selected positions of the non-magnified image.
Figure 4B:
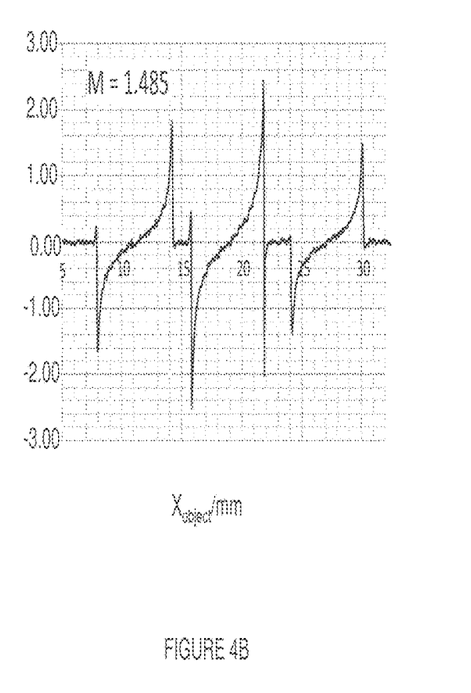
FIG. 4B schematically illustrates the phase contrast signal intensity at the same selected positions of the magnified image.

Further reference is made to FIG. 4A, which schematically illustrates the phase contrast signal intensity at selected positions of non-magnified image 200A; and to FIG. 4B which schematically illustrates the phase contrast signal intensity at the same selected positions of magnified image 200B.

The phase contrast signal intensity may for example be determined for a particular row of matrix image data and for all column values. Such a selection of image data is schematically illustrated with dashed lines 204A and 204B, both of which have the same vertical position with respect to, e.g., absorption grating 123 or any other optical component of X-ray interferometer 100. Correspondingly, dashed line 204A represents a first set of image data, and dashed line 204B represents a second set of image data for a selected horizontal cross-section of non-magnified image 200A and magnified image 200B, respectively. Dashed lines 204A and 204B are at some instances hereinafter also referred to as first image data set 204A and second image data set 204B, respectively. Both first image data set 204A and second image data set 204B are selected at identical positions of image matrix.

As can readily be seen from FIGS. 4A and 4B, apart from the different level of noise, the respective phase contrast signal intensity of first image data set 204A is almost identical to phase contrast signal intensity of second image data set 204B, despite the magnification by M equaling about 1.485.

In other words, the difference in the phase contrast signal intensities for, e.g., M equaling about 1 and M equaling about 1.485 is negligibly small. It may follow from the aforesaid that even for significant magnification by, for example, about 150%, the phase contrast signal intensity of the magnified image remains substantially unchanged.

In FIGS. 4A and 4B, the horizontal axis X (position coordinate denoted "$X_{object}$/mm"), which represents a lateral position along the field of view, was scaled such that the profiles of the plastic rods match their thickness or width in the image plane (approx. 6 mm). The vertical axis, which represents the amplitude of the differential phase contrast signal, is non-scaled to the height of the plastics in the image plane.

Performance comparison regarding magnification M and phase contrast sensitivity S Tables 1 to 4 compare X-ray interferometer 100 configurations against conventional X-ray interferometers. The parameters outlined herein regarding X-ray interferometer 100 are by no means to be construed as limiting and thus do not limit the scope of what is disclosed herein.

For all setups exemplified below in the Tables 1 to 4 below, the following parameters may apply:

$L_{tot}$ equaling about 1.5 m, which denotes the distance from the focal spot of X-ray source 110 to sensor plane of detector 140, Operating energy of the source substantially equals about 20 keV, and the Fractional Talbot order is n=4.

Furthermore, for the conventional approach it is assumed that the total length of the setup obeys $L_{tot}$=L+d.

The phase contrast sensitivity S, measured in [rad$^{-1}$], may be determined, for example, as outlined by T. Donath, M. Chabior, F. Pfeiffer, O. Bunk, E. Reznikova, J, Mohr, E, Hempel, S, Popescu, M, Hoheisel, M, Schuster, J. Baumann, and C. David, in "Inverse geometry for grating-based x-ray phase-contrast imaging", J. Appl. Phys. 106, 054703 (2009).

In the conventional X-ray interferometers exemplified herein below, the gratings are relatively close to detector 140, e.g. absorption grating 123 is directly in front of detector 140. Therefore, the grating area of absorption grating 123 is required to substantially cover the entire sensor field of detector 140, whereas for X-ray interferometer 100, the required area of absorption grating 123 scales with the magnification factor M when compared to the area of the field of view of detector 140.

In the examples outlined below with respect to Table 1 and Table 2 it is assumed that the distance between the gratings is identical (e.g., about 10 cm):

TABLE 1

Comparison setup I (Magnification M equals about 5):

| | $P_1$ [μm] | $P_2$ [μm] | l [cm] | d [cm] | $d_s$ [cm] | $d_M$ [cm] | S [rad$^{-1}$] |
|---|---|---|---|---|---|---|---|
| Conventional X-ray interferometer | 3.41 | 3.65 | 140.0 | 10.0 | 110 | 0 | 59 |
| X-ray interferometer 100 | 3.0 | 3.96 | 30.0 | 10.0 | 0 | 110 = (140 − 30) | 253 |

TABLE 2

Comparison setup II - Magnification M equals about 10:

| | $P_1$ [μm] | $P_2$ [μm] | l [cm] | d [cm] | $d_s$ [cm] | $d_M$ [cm] | S [rad$^{-1}$] |
|---|---|---|---|---|---|---|---|
| Conventional X-ray interferometer | 3.41 | 3.65 | 140.0 | 10.0 | 125 | 0 | 29 |
| X-ray interferometer 100 | 2.73 | 4.55 | 15.0 | 10.0 | 0 | 125 = (150 − 15 − 10) | 220 |

The grating periods $P_1$ and $P_2$ are of the same order of magnitude for both the conventional X-ray interferometer and X-ray interferometer 100. However, the phase contrast sensitivity is considerably higher for X-ray interferometer 100 than for the conventional X-ray interferometer by, for example, a multiplicative factor ranging, for example, from about 1.1 to about 10 or higher. An increase in the multiplicative factor of the phase contrast sensitivity may be, for example, about at least 1.2, about at least 1.3, about at least 1.5, about at least 2, about at least 1.5, about at least 3.5, about at least 4, about at least 5, about at least 6, about at least 7, about at least 7.5, about at least 8, about at least 9 or about at least 10. Phase contrast sensitivities that may be attainable with X-ray interferometer 100 may be for example, range from about 150 to about at least 300 and, for example, attain values of about at least 160, about at least 170, about at least 180, about at least 190 at about least at least 200, about at least 210, about at least 220, about at least 230, about at least 240, about at least 250, about at least 260, about at least 270, about at least 280 or about at least 290.

Referring now to Tables 3 and 4, grating period $P_1$ was adjusted such that the sensitivity S becomes substantially equal for both the conventional X-ray interferometer and X-ray interferometer 100. Furthermore, for X-ray interferometer 100 parameter $P_1$ was set as about 3 μm, which may then define the other parameters for X-ray interferometer 100.

TABLE 3

Comparison III - Magnification M equals about 5

| | $P_1$ [μm] | $P_2$ [μm] | l [cm] | d [cm] | $d_s$ [cm] | $d_M$ [cm] | S [rad$^{-1}$] |
|---|---|---|---|---|---|---|---|
| Conventional X-ray interferometer | 6.8 | 15.1 | 67.5 | 82.5 | 37.5 | 0 | 242 |
| X-ray interferometer 100 | 3.0 | 3.96 | 30.0 | 10.0 | 0 | 110 | 242 |

TABLE 4

Comparison IV - Magnification M equals about 10

| | $P_1$ [μm] | $P_2$ [μm] | l [cm] | d [cm] | $d_s$ [cm] | $d_M$ [cm] | S [rad$^{-1}$] |
|---|---|---|---|---|---|---|---|
| Conventional X-ray interferometer | 5.14 | 30.0 | 26.0 | 124.0 | 11 | 0 | 242 |
| X-ray interferometer 100 | 3.0 | 5.8 | 15.0 | 14.0 | 0 | 121 | 242 |

As can readily be derived from the data in Table 3 and Table 4, the attained phase contrast sensitivity is the same for M equaling about 5 and M equaling about 10 for both the conventional X-ray interferometer and X-ray interferometer 100. Although for the conventional X-ray interferometer, object 130 is positioned such that $d_s>0$, substantially the same phase contrast sensitivity is attained by X-ray interferometer 100, where object 130 is positioned directly in front of phase grating 122 ($d_s$ substantially equals 0). This is because the grating periods $P_1$ and $P_2$ of the conventional X-ray interferometer are considerably larger than in X-ray interferometer 100, which offsets any loss in phase contrast sensitivity which would otherwise occur for ds>0 and for $d_M$ that substantially equals 0.

In embodiments, grating periods for $P_1$ and $P_2$ in X-ray interferometer 100 may be substantially smaller than in known phase grating imaging systems where $d_M$ equals about 0. Its width can therefore be smaller sized than those of substantially non-magnifying X-ray interferometer. For example, $P_1$ and $P_2$ may be equal or less than about 6 μm, 5 μm, 4 μm, or 3 μm, for $d_M>0$ and, optionally, when $d_s$ is as small as possible. As a consequence, X-ray interferometer 100 may be relatively compact in size. Moreover, since a change in the multiplicative factor M may be attained by altering $d_M$ instead of $d_s$, it is not required that X-ray interferometer 100 based on, e.g., Talbot grating interferometer, features a large distance d between the gratings in order to achieve the magnification. In embodiments, the distance between phase grating 122 and absorption grating 123 in X-ray interferometer 100 may be less than half of the total setup length $L_{tot}$.

Any of the above-outlined embodiments, examples and implementations of X-ray interferometer 100 are applicable in conjunction with dark-field X-ray imaging.

In terms of visible-light Fourier optics, dark-field illumination removes the zeroth order (unscattered light) from the diffraction pattern formed at the rear focal plane of the objective lens for obtaining an image that is formed exclusively from higher-angle diffraction intensities scattered by the specimen. Quite similarly, when employing, according to embodiments, dark-field illumination with X-ray interferometer 100, information about the scattering power of object 130 is contained in the higher order of the intensity oscillation respective of each pixel of detector 140. The intensity oscillation is responsive to angle scattering in object 130 which might occur as a consequence of microstructuring of object 130. X-ray interferometer 100 can thus provide images representing X-ray angle scattering that might be caused by object 130. Microstructures may for example be attributed to porosity of at least some of object 130.

In some embodiments, phase contrast imaging system may also provide a conventional X-ray attenuation image.

In the discussion unless otherwise stated, terms such as "substantially", "at least approximately" and "about" modifying a condition or relationship characteristic of a feature or features of an embodiment of the invention, are understood to mean that the condition or characteristic is defined to within tolerances that are acceptable for operation of the embodiment for an application for which it is intended.

It should be understood that an embodiment is an example or implementation of embodiments. The various appearances of "one embodiment," "an embodiment" or "some embodiments" do not necessarily all refer to the same embodiments.

Although various features may be described in the context of a single embodiment, the features may also be provided separately or in any suitable combination. Conversely, features may be described herein in the context of separate embodiments for clarity, these features may also be implemented in a single embodiment.

Reference in the specification to "one embodiment", "an embodiment", "some embodiments" or "other embodiments" means that a particular feature, structure, or characteristic described in connection with the embodiments is included in at least one embodiment, but not necessarily all embodiments. It should be understood that the phraseology and terminology employed herein is not to be construed as limiting and is for descriptive purpose only.

The principles and uses of the teachings of the embodiments may be better understood with reference to the accompanying description, figures and examples. It should be understood that the details set forth herein do not construe a limitation to an application of the disclosed embodiments. Furthermore, it should be understood that the embodiments can be carried out or practiced in various ways and that the system and/or method can be implemented with embodiments other than the ones outlined in the description herein.

It should be understood that the terms "including", "comprising", "consisting" and grammatical variants thereof do not preclude the addition of one or more components, features, steps, integers or groups thereof.

The meaning of "in" includes "in" and "on". The term "based on" is not exclusive and provides for being based on additional factors not described, unless otherwise indicated.

If the specification or claims refer to "an additional" element, that does not preclude there being more than one of the additional element.

It should be understood that where the claims or specification refer to "a" or "an" element, such reference is not to be construed as there being only one of that element.

It should be understood that where the specification states that a component, feature, structure, or characteristic "may", "might", "can" or "could" be included, that particular component, feature, structure, or characteristic is not required to be included.

The term "method" and "process" refers to manners, means, techniques and procedures for accomplishing a given task including, but is not limited to those manners, means, techniques and procedures either known to, or readily developed from known manners, means, techniques and procedures by practitioners of the art to which the disclosed system and method belong.

The descriptions, examples, methods and materials presented in the claims and the specification are not to be construed as limiting but rather as illustrative only.

The disclosed embodiments can be implemented in the testing or practice with methods and materials equivalent or similar to those described herein.

It should be noted that the discussion that values or measures disclosed herein above should by no means to be construed as limiting and are for exemplary purposes only.

Descriptions of embodiments in the present application are provided by way of example and are not intended to limit the scope of the embodiments. The described embodiments comprise different features, not all of which are required in all embodiments. Some embodiments utilize only some of the features or possible combinations of the features. Variations of embodiments that are described, and embodiments comprising different combinations of features noted in the disclosure, will occur to persons of the art.

The invention claimed is:

1. A method for performing phase contrast imaging with an X-ray interferometer that is operative to irradiate an object with X-ray at a given radiation energy, the X-ray interferometer having a total setup length $L_{tot}$, the method comprising:
   a detector detecting radiation emitted by an X-ray source with a projection magnification M greater than 1 and having a sensor plane, wherein the total setup length $L_{tot}$ is a distance from a focal spot of the X-ray source to a plane of the detector;
   a phase grating phase-shifting X-ray emanating from the object and which is incident onto the phase grating;
   an absorption grating intensity modulating the phase-shifted X-ray from the phase grating;
   positioning the phase grating between the X-ray source and the absorption grating at a distance l from the X-ray source;
   positioning the absorption grating between the phase grating and the detector at a distance d from the phase grating;
   positioning the detector at a distance $d_M$ from the absorption grating, the distance $d_M$ being at least 5 cm and up to 2 meters, and the distance d being less than half the total setup length $L_{tot}$, where $$M = \frac{d_M + d + 1}{1 - d_s};$$

positioning the object between the X-ray source and the phase grating at a distance $d_s$ from the phase grating, the distance $d_s$ being a distance between the phase grating and the plane which is perpendicular to an optical axis and intersects a geometric center of the object;
   dimensioning the grating period of the phase grating and the grating period of the absorption grating such that, $$d = \frac{n.\eta.p_1.p_2}{8.\lambda} \text{ and}$$

$$l = d.\frac{p_1}{\eta.p_2 - p_1}$$

where λ denotes a wavelength of the X-ray emitted by the X-ray source, n denotes a fractional Talbot order, η denotes a symmetry parameter, $p_1$ denotes the grating period of the phase grating and $p_2$ denotes the grating period of the absorption grating; and
   dimensioning $d_s$ and $d_m$ so that a phase contrast sensitivity of an image of the object detected by the detector is not reduced with M greater than 1.

2. The method according to claim 1, further comprising positioning the object at a distance from the phase grating which substantially equals zero.

3. The method according to claim 1, further comprising dark-field illuminating the object to obtain a dark-field image thereof.

4. The method according to claim 1, wherein the X-ray interferometer is implemented as a Talbot-Lau interferometer.

5. The method according to claim 1, wherein the X-ray interferometer is implemented as a Talbot interferometer.

6. The method according to claim 1, wherein the X-ray interferometer is operative at a fractional Talbot order of n=4.

7. The method according to claim 1, further comprising laterally extensioning the phase grating, the absorption grating and the detector to cover a diverging field size of the X-ray emanating from the imaged object.

8. The method according to claim 1, wherein during imaging, the distance between the object and the phase grating substantially equals zero.

9. The method according to claim 1 further comprising laterally dimensioning the phase grating and the absorption grating to allow for selecting the distance between the detector and the absorption grating to obtain, when imaging the object, a corresponding change in the projection magnification M between lateral dimensions of the image of the object and the object itself.

10. The method according to claim 8, wherein the projection magnification M ranges from more than 1 to about at least 50.

11. The method according to claim 1, wherein the grating period of the phase grating is equal or less than about 5 μm.

12. The method according to claim 1, wherein the grating period of the absorption grating is equal or less than about 5 μm.

13. The method according to claim 1, wherein the gratings periods of the absorption and phase grating are dimensioned such that the distance between the phase grating and absorption grating is small compared to the distance between the detector and the absorption grating and the distance between the source and the phase grating.

14. The method according to claim 1, wherein lateral dimensions of the phase grating, the absorption grating and the detector are dimensioned such to cover a diverging field size of the X-ray emanating from the imaged object and wherein, during imaging, the distance between the object and the phase grating substantially equals zero.

15. The method according to claim 1, wherein the gratings periods of the absorption and phase grating are dimensioned such that the distance between the phase grating and absorption grating is small compared to the distance between the source and the phase grating.

16. The method according to claim 1, wherein the gratings periods of the absorption and phase grating are dimensioned such that the distance between the phase grating and absorption grating is small compared to the distance between the detector and the absorption grating and the distance between the source and the phase grating, and wherein, during imaging, the distance between the object and the phase grating substantially equals zero.

* * * * *